United States Patent [19]
Boyd et al.

[11] Patent Number: 5,707,988
[45] Date of Patent: Jan. 13, 1998

[54] BENZO[D] ISOXAZOLE DERIVATIVES, COMPOSITIONS CONTAINING THEM AND THEIR USE IN THERAPY

[75] Inventors: Edward Andrew Boyd, Purley; Brenda Costall, Addingham; Mary Elizabeth Kelly, Thornton; Philip James Parsons, Reading, all of England

[73] Assignee: British Technology Group Ltd., London, England

[21] Appl. No.: 464,709

[22] PCT Filed: Dec. 7, 1993

[86] PCT No.: PCT/GB93/02501

§ 371 Date: Jul. 11, 1995

§ 102(e) Date: Jul. 11, 1995

[87] PCT Pub. No.: WO94/14816

PCT Pub. Date: Jul. 7, 1994

[30] Foreign Application Priority Data

Dec. 23, 1992 [GB] United Kingdom ............... 9226857

[51] Int. Cl.$^6$ .................. A61K 31/54; A61K 31/535; C07D 498/04; C07D 513/04
[52] U.S. Cl. .................. 514/224.5; 514/230.2; 514/250; 514/291; 544/32; 544/101; 544/346; 546/89; 546/92
[58] Field of Search ............... 544/32, 101, 346; 546/89, 92; 514/224.5, 230.2, 250, 291

[56] References Cited

U.S. PATENT DOCUMENTS

| | | | |
|---|---|---|---|
| 4,452,799 | 6/1984 | Temple et al. | 424/250 |
| 5,049,564 | 9/1991 | DeBernardis et al. | 514/290 |
| 5,114,936 | 5/1992 | Wettlaufer et al. | 514/233.8 |
| 5,476,867 | 12/1995 | Boyd et al. | 514/379 |

FOREIGN PATENT DOCUMENTS

| | | |
|---|---|---|
| 3247 530 A1 | 6/1983 | Germany . |
| 1540580 | 2/1979 | United Kingdom . |
| WO 90/14342 | 11/1990 | WIPO . |

OTHER PUBLICATIONS

J.F. Elsworth et al. "Nitrones. Part IX. the Synthesis and Reactions. . . " Journal of the Chemical Society, Section C, No. 19, 1968, Letchworth GB, pp. 2423–2427.

S. Mzengeza et al. "Dipolar cycloaddition reactions. . . " Journal of the Chemical Society, Chemical Communications 194. Letchworth, GB, pp. 606–607.

A. Vasella. "Stereoselektivtat und. . . " Helvitica Chimica Acta, vol. 60 No. 4, 1 Jun. 1966, Basel CH, pp. 1273–1295.

J.T. Bailey et al. "Annelation of cyclic dienes to amino. . . " Journal of Organic Chemistry, vol. 47 No. 5, 26 Feb. 1982, Easton, US, pp. 857–863..

*Primary Examiner*—Philip I. Datlow
*Attorney, Agent, or Firm*—Nixon & Vanderhye

[57] ABSTRACT

Compounds of formula (I)

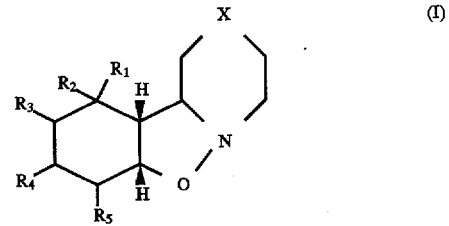

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, the compound optionally being in the form of a salt thereof formed with a physiologically acceptable inorganic or organic acid, are of value for the treatment of anxiety and in the improvement of learning ability and/or the reversal of amnesia.

17 Claims, 3 Drawing Sheets

BENZO[D] ISOXAZOLE DERIVATIVES, COMPOSITIONS CONTAINING THEM AND THEIR USE IN THERAPY

This application is the national stage application under 35 USC 371 of PCT/GB93/02222501 filed Dec. 7, 1993. This invention relates to psychoactive compounds of value in the treatment of anxiety and in the improvement of learning ability and the reversal of amnesia.

DESCRIPTION OF THE INVENTION

Accordingly the present invention comprises a compound of formula (I)

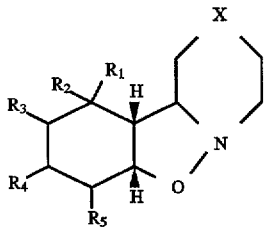

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, the compound optionally being in the form of a salt thereof formed with a physiologically acceptable inorganic or organic acid, for use in therapy.

The invention further comprises the compounds per se of formula (I) as just defined with the exception of the compound in which X is >O and each of $R_1$ to $R_5$ is hydrogen which has been described by Elsworth and Lamchen (Journal of the Chemical Society, C, 1968, 19, 2423–7) as a compound produced in an investigation of the reactions of 2,3-dihydro-1,4-oxazine-4-oxide.

The system of numbering used herein is based on that of the fused benzo[d]isoxazole ring system as shown below

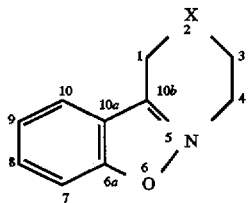

The standard method is used for indicating stereochemistry in formula (I), i.e. a thickened line represents a bond projecting upwardly from the plane of the paper. It will be seen that the compounds of the present invention therefore have cis stereochemistry with respect to the relative orientation of the hydrogen atoms at positions 6a and 10a.

When X is a group >NR, an alkyl group R or the alkyl portion of a phenalkyl group R may be straight or branched chain but is preferably the former and the phenyl group of a phenalkyl group R is preferably terminally substituted on the alkyl group. Although the alkyl group or alkyl portion of a phenalkyl group may be of 1, 2, 3, 4, 5 or 6 carbon atoms, it is preferably of a size at the lower end of this range, for example being a propyl, ethyl or especially a methyl group or such a group terminally substituted by a phenyl group. Compounds containing a group X of the form >NR in which R is phenyl are also of some interest. In general, however, the preferred group X is >O.

The groups $R_1$ and $R_2$ are preferably either together an oxo group or $R_1$ is hydrogen and $R_2$ together with $R_3$ is the second bond of a double bond joining positions 9 and 10. Alternatively, when $R_1$ is hydrogen but $R_2$ and $R_3$ are not a bond, either $R_3$ and $R_4$ may be the second bond of a double bond joining positions 8 and 9 or $R_4$ and $R_5$ may be the second bond of a double bond joining positions 7 and 8. However, it is preferred that, where the one optional double bond in the six membered ring is present, it joins positions 9 and 10 so that $R_4$ and $R_5$ are usually each hydrogen.

Examples of specific compounds of use in the present invention are those containing a combination of the preferences for X and $R_1$ to $R_5$ indicated above, for example the compounds in which (1) X is >O, $R_1$ and $R_2$ are =O, and $R_3$ $R_4$ and $R_5$ are H: cis-1,3,4,6a,7,8,9,10,10a,10b-decahydro-1,4-oxazno-[4,3-b]benz[d]isoxazol-10-one;

(2) X is >O, $R_1$ is H, $R_2$ and $R_3$ are a bond, and $R_4$ and $R_5$ are H: cis-1,3,4,6a,7,8,10a,10b-octahydro-1,4-oxazino[4,3-b]benz[d]isoxazol;

(3) X is >NR where R is methyl or phenyl, $R_1$ and $R_2$ are =O, and $R_3$, $R_4$ and $R_5$ are H: cis-2-methyl- or -phenyl-2,3,4,6a,7,8,9,10,10a,10b-decahydro-1H-pyrazino[1,2-b]benz[d]isoxazol-10-one; and (4) X is >NR where R is methyl or phenyl, $R_1$ is H, $R_2$ and $R_3$ are a bond, and $R_4$ and $R_5$ are H: cis-2-methyl- or phenyl-2,3,4,6a,7,8,10a,10b-octahydro-1H-pyrazino-[1,2-b]benz[d]isoxazole Of these, compound (2) and especially compound (1) are of particular interest.

As indicated, the compound of formula (I) may exist in the form of an amine type salt formed with a physiologically acceptable inorganic or organic acid. A preferred acid is hydrochloric acid but other acids which may be used include hydrobromic, sulphuric, nitric, phosphoric, isethionic, acetic, fumaric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic acid. In general, however, use of the free base rather than a salt is preferred.

Although the stereochemistry of the molecule is in part indicated in formula (I), the hydrogen atom at position 10b may adopt one of two orientations relative to the two hydrogen atoms at positions 6a and 10a. It is preferred, however, that these three hydrogen atoms are similarly disposed in the cis configuration. Thus, the preferred form of each of the specific compounds (1) to (6) hereinbefore may be identified as having the relative stereochemistry 6aR*, 10aS*,10bS* (the lowest numbered position, position 6a, being assigned the R* configuration). Moreover, it will be appreciated that the compounds according to the invention will be resolvable into enantiomeric forms, one of which may be of particular value by virtue of its level of therapeutic activity and/or physical properties such as greater aqueous solubility, etc.

The compounds of formula (I) may be prepared by a number of alternative routes. In a first process a compound of formula (II) is reacted with a compound of formula (III)

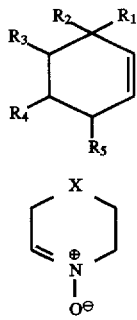

(II)

(III)

in which $R_1$ to $R_5$ and X are as defined for the compound of formula (I). A second, preferred process for the preparation of compounds of formula (I) involves the formation of the compound of formula (III) in situ through the use of a compound of formula (IIIa), which is converted to the compound of formula (III) through the use of tungstate catalysed oxidation.

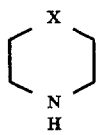

(IIIa)

It will be appreciated, however that the compounds of formula (I) may also be prepared by modifications of these processes and by other alternative processes which will be apparent from the chemical art. In particular it may be possible to modify the group X in an initially obtained product to that present in the desired product of formula (I), for example through the conversion of a group X of the form >NR wherein R is hydrogen to one in which it is not hydrogen.

The first mentioned process generally requires heating of the reactants together, for example at 70°–100° C. in a sealed tube under an inert gas such as nitrogen for a period of 14 to 24 hours. However, when the N-oxide is alternatively generated in situ by oxidation of the corresponding secondary amine, for example with pertungstic acid, the reaction with the compound (II) may be effected at room temperature.

When the compound of formula (I) is in salt form, such salts may be prepared from the free base by treatment with the appropriate acid, either in a polar solvent such as water, if necessary with the application of heat, or more conveniently generating an acid such as hydrochloric acid in situ in a non-aqueous solvent, for example methanol.

The compounds of formula (I) are of value for the treatment of anxiety, being of particular interest for the treatment of anxiogenesis caused by withdrawal from benzodiazepines such as diazepam as they exhibit cross tolerance with these benzodiazepines in comparison with buspirone, for example, which does not. The compounds (I) are also of interest for the treatment of anxiogenesis caused by abruptly ceasing administration of drugs of abuse and in particular nicotine, alcohol and cocaine.

The compounds of formula (I) are alternatively of value for use in the improvement of learning and/or the reversal of amnesia, for example amnesia arising from Alzheimer's disease or vascular dementias.

The dose rates required to achieve effective anxiolysis, improvement in learning ability or reversal of amnesia will of course vary with the mammal treated, the mammal's body weight, surface area, age and general state of health, but as a guide it may be stated that in human patients a suitable dose for parenteral administration is in the range of 0.001 ng/kg to 10 mg/kg, particularly 1 ng/kg to 1 mg/kg, and for oral administration is in the range of 1 µg/kg to 10 mg/kg, particularly 10 µg/kg to 1 mg/kg and especially 10 µg/kg to 100 µg/kg, and that other mammals may be treated on a similar mg/kg basis. Such doses may be repeated as desired, for example 2 to 3 times a day during the period of treatment. Doses outside these ranges may also be given if appropriate. In general the improvement of learning ability and/or the reversal of amnesia requires somewhat lower doses within the ranges given than the treatment of anxiety.

Administration may be by mouth or, less usually, parenterally (including subcutaneously, intramuscularly and intravenously) or topically.

Whilst it is possible for the compound (I) to be administered alone it is preferable to present it in a pharmaceutical composition. Compositions of the present invention for medical use comprise one or more of the active compounds (I) together with one or more pharmaceutically acceptable diluents or carriers and, optionally, other therapeutic ingredients. The diluent(s) or carrier(s) should be pharmaceutically acceptable in the sense of being compatible with the other ingredients of the formulation and not deleterious to the recipient thereof.

Compositions include those suitable for oral, parenteral or topical administration. The formulations may conveniently be presented in unit dosage form and may be prepared by any of the methods well known in the art of pharmacy. In general, formulation includes the step of bringing the active compound(s) (I) into association with a diluent or carrier and, where appropriate, one or more accessory ingredients. Usually, the formulations are prepared by bringing the active compound uniformly and intimately into association with a liquid or with a finely divided solid or with both and then, where appropriate, shaping the product into desired formulations.

Compositions of the present invention suitable for oral administration may conveniently be presented as discrete units such as capsules, cachets, tablets or lozenges, each containing a predetermined amount of the active compound, for example as a powder or granules, or as a solution or a suspension in an aqueous liquid or non-aqueous liquid such as a syrup, an elixir, an emulsion or a draught. The compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Compositions suitable for parental administration conveniently comprise a sterile aqueous preparation of the active compound which is preferably isotonic with the blood of the recipient.

Other types of composition include aerosols and suppositories.

BRIEF DESCRIPTION OF THE DRAWINGS

The invention is further illustrated with reference to the following Examples and accompanying drawings, in which.

EXAMPLES

Figure 1:
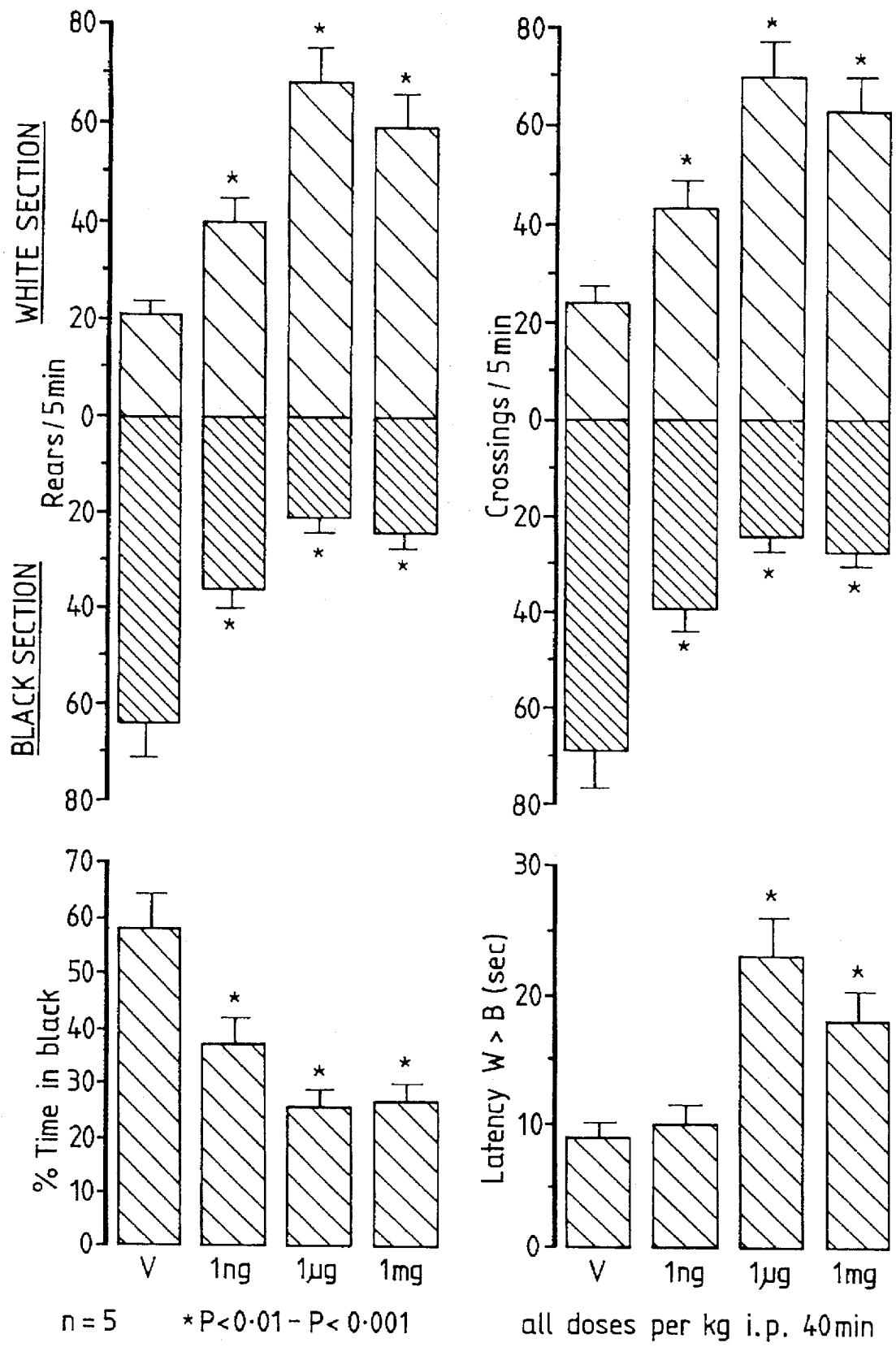
FIG. 1 shows the results of studies of a compound of the invention for anxiolytic activity using the black and white box test.

The compound of Example 1 is believed to have the stereochemistry rel-(6aR*, 10aS*, 10bS*), which indicates that the hydrogen atom at the 10b position is similarly orientated relative to the two cis hydrogen atoms at positions 6a and 10a.

Example 1: Preparation of cis-1,3,4,6a,7,8,9,10,10a,10b-decahydro-1,4-oxazino-[4,3-b]benz[d]isoxazol-10-one To a solution of morpholine (3.1 ml, 35 mmol) and sodium tungstate dihydrate (0.46 g, 1.4 mmol) in water (7 ml) was cautiously added dropwise a solution of hydrogen peroxide (ca. 27.5%) (8.7 ml, ca. 80 mmol) over approximately 30 minutes using an ice bath to keep the reaction temperature below 25° C. After 20 minutes of stirring at 0° C., 2-cyclohexenone (3.53 g, 36.8 mmol) was added and the solution was then stirred under nitrogen for 24 hours at room temperature. After 24 hours the reaction mixture was extracted with dichloromethane (3×75 ml) and the organic extracts were combined and washed with water (1×30 ml), saturated sodium bicarbonate solution (1×30 ml) and saturated brine (1×40 ml), followed by drying over anhydrous magnesium sulphate. After filtration the solvents were removed in vacuo to give a viscous light brown oil (5.4 g, 78%) which partially crystallised at −20° C. and remained crystalline at room temperature. The title compound was purified by flash chromatography using 5:1 v/v ethyl acetate-:petroleum ether (b.p. 40°–60° C.) as the solvent system. The product had an Rf of 0.33 and was isolated as a pure white crystalline solid (1.72 g, 25%) [with a further quantity (4.12 g, 60%) being obtained as a solid which contained a minor contaminant], $v_{max}$ (film in $CH_2Cl_2$) 2941, 2866, 1702, 1697, 1124 $cm^{-1}$; $\delta_H$ (250 MHz; $CDCl_3$-$Me_4Si$) 1.70–1.85 (2 H, m), 1.85–2.05 (4 H, br m), 2.30–2.50 (4 H, br m), 2.80–2.95 (1 H, m), 3.00–3.10 (1 H, m), 3.80–3.95 (2 H, m), 4.75–4.85 (1 H, m); M/z 197 ($MH^+$ 100%) (Found: $M^+$ 197.1052; $C_{10}H_{15}NO_3$ requires $MH^+$ 19.1052).

Example 2: Preparation of cis-1,3,4,6a,7,8,10a,10b-octahydro-1,4-oxazino[4,3-b]benz[d]isoxazol Using the procedure of Example 1, the nitrone produced by the reaction of morpholine and hydrogen peroxide in the presence of sodium tungstate dihydrate is reacted with cyclohexene in place of 2-cyclohexenone. The reaction mixture is worked up as described in Example 1 to provide the title compound as a low melting point solid with i.r. and n.m.r. spectra generally corresponding to those quoted by Elsworth and Lamchen, ibid: $v_{max}$ (film) 1462, 1273, 1129, 861 $cm^{-1}$; $\delta_H$ 5.6 (1H), 6.2 (2H), 7.0 (3H), 7.4 (1H) and 8.4 (8H).

Example 3: Tests of Physiological Activity Drugs

The compound of Example 1 was suspended in a minimum quantity of polyethylene glycol (PEG) and diluted with distilled water. Scopolamine hydrobromide was dissolved in saline. All drugs were administered in a volume of 1 ml/100 g (mouse).

(1) ANXIOLYTIC ACTIVITY

The compound of Example 1 was tested for anxiolytic activity using the black and white box test.

Naive BKW male albino mice (Bradford bred) of 30–35 g were used in all studies. 10 mice were normally housed in each cage and kept for at least two weeks on a 12 hour light/dark cycle with lights off at 07.00 h. Behavioural testing was conducted between 13.00–18.00h in a darkened room illuminated with red light. Mice were taken from the dark holding room to the testing room in an enclosed trolley and allowed at least 1 hour for adaptation to the new environment.

The apparatus used for the detection of changes in exploratory behaviour consisted of an open-topped box (45×27×27 cm high) lined into 9 cm squares, two-fifths painted black and illuminated under a dim red light (1×60 W) and partitioned from the remainder of the box which was painted white and brightly illuminated with a 60 W light source located 17 cm above the box. An opening 7.5×7.5 cm located at floor level in the centre of the partition allowed access between the two compartments. At the start of testing mice were placed individually into the centre of the white, brightly lit area of the test box.

The mice were observed over a 5 minute period by remote video recording and four behaviours noted: (i) the number of exploratory rearings in the white and black sections, (ii) the number of line crossings in the white and black areas, (iii) the time spent in the white and black areas and (iv) the latency of the initial movement from the white to the black area.

In initial studies, separate groups of naive mice received the vehicle only or the compound at 1 ng/kg, 1 μg/kg or 1 mg/kg i.p. 40 minutes before exposure to the black:white test box.

Mice were used once only in treatment groups of 5. Results were analysed using single factor ANOVA followed by Dunnett's t-test for comparing multiple treatments with a single control. The changes in the four behaviours, as compared with administration of the vehicle only (V), are illustrated in FIG. 1 for each of the three dose levels. An anxiolytic effect is evidenced by an enhanced preference for the white area as compared with the black area which is that preferred under normal conditions. It will be seen from the Figure that the compound administered by the intraperitoneal route at each dose of 1 ng/kg, 1 μg/kg and 1 mg/kg produced changes in behaviour indicative of an anxiolytic potential for the compound, although the effect increased significantly on increasing the dose from 1 ng/kg.

(2) IMPROVEMENT OF LEARNING AND REVERSAL OF SCOPOLAMINE-INDUCED AMNESIA

The compound of Example 1 was initially tested at sub anxiolytic doses of 0.1 ng/kg but little effect was observed and the procedure was therefore repeated using a dose of 1 ng/kg which is one found to produce only a low level anxiolytic effect.

The following procedure was employed:

Mouse habituation test

The studies used male albino (BKW) mice initially weighing 27–35 g (young adult mice of 6–8 weeks). In their home room mice were housed in groups of 10 and were given free access to food and water. The mice were kept at a 12 hour light and 12 hour dark cycle with lights off at 7.00 a.m. and on at 7.00 p.m.

The test apparatus consisted of an open-topped box (45×27×27 cm) one third painted black and illuminated under a dim red light (1×60 W) and partitioned from the remainder of the box which was brightly illuminated with a 100 W light source located 17 cm above the box. Access between these two areas was enabled by means of a 7.5×7.5 cm opening located at floor level in the centre of the partition (which also served to prevent diffusion of light between the two compartments of the test box). The floor area was lined into 9 cm squares.

The habituation test was carried out daily by placing mice in the centre of the white section of the test box (mice taken from dark home environment in a dark container, to the experimental room maintained in low red lighting, and would normally be averse to the bright white conditions). Testing was carried out between 8.30 a.m. and 12.30 p.m. The test period was 5 minutes per day. Behaviour was assessed via remote video recording, and the following measurements taken:

1. Latency to move from the white to the black section (sec).
2. Numbers of exploratory rears in the white and black sections during the 5 minute tests.
3. Numbers of line crossings (exploratory locomotion) in the white and black sections during the 5 minute test.
4. % Time spent in the black section of the box during the 5 minute test.
5. Numbers of transitions between the black and white sections of the test box during the 5 minute test (since this parameter was not changed in any situation in the present studies, data for transitions is not given or commented on further).

On repeated daily exposure to the box the mice habituate to the test situation by moving rapidly into the black area where they spend most time and exhibit most behaviour (measured as exploratory rears and crossings of lines marked on the test box floor). Generally, the habituation process occurs over a 4–6 day period and, for example latency for the initial movement from the white to the black section is reduced from initial values of 10–12 seconds to 1–4 seconds by the 5th–6th day of test.

Figure 2:
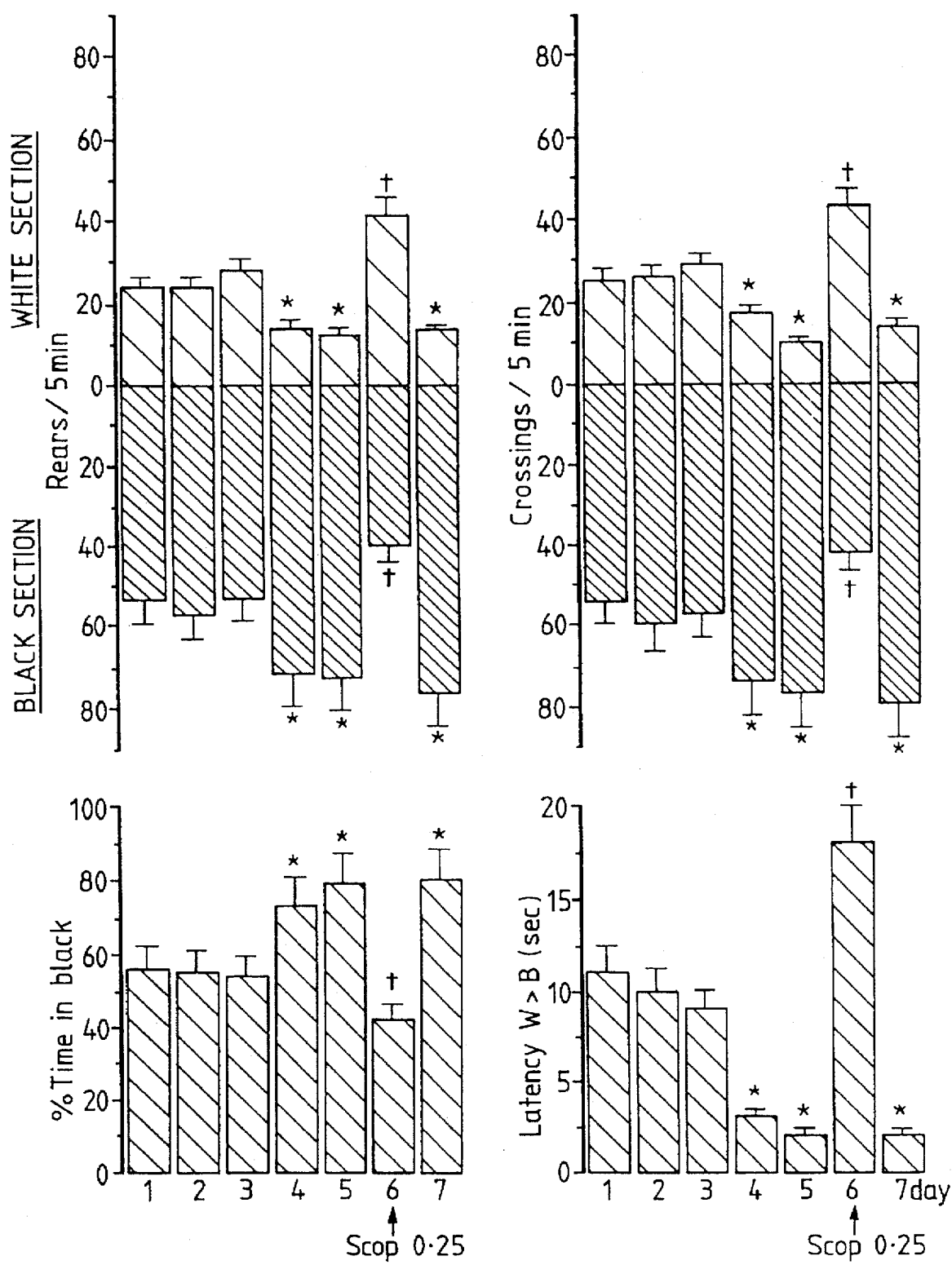
FIGS. 2 and 3 show the results of the mouse habituation test demonstrating improvement of learning ability and reversal of scopolomine-induced amnesia.

The habituation profile of the mice was disrupted by acute scopolamine (0.25 mg/kg i.p., 40 minutes before test) (dose carefully selected as minimally effective, without interference from peripheral effects as checked by assessments of the actions of the same dose of methylscopolamine). The behaviour of the control group of mice is illustrated in FIG. 2.

Figure 3:
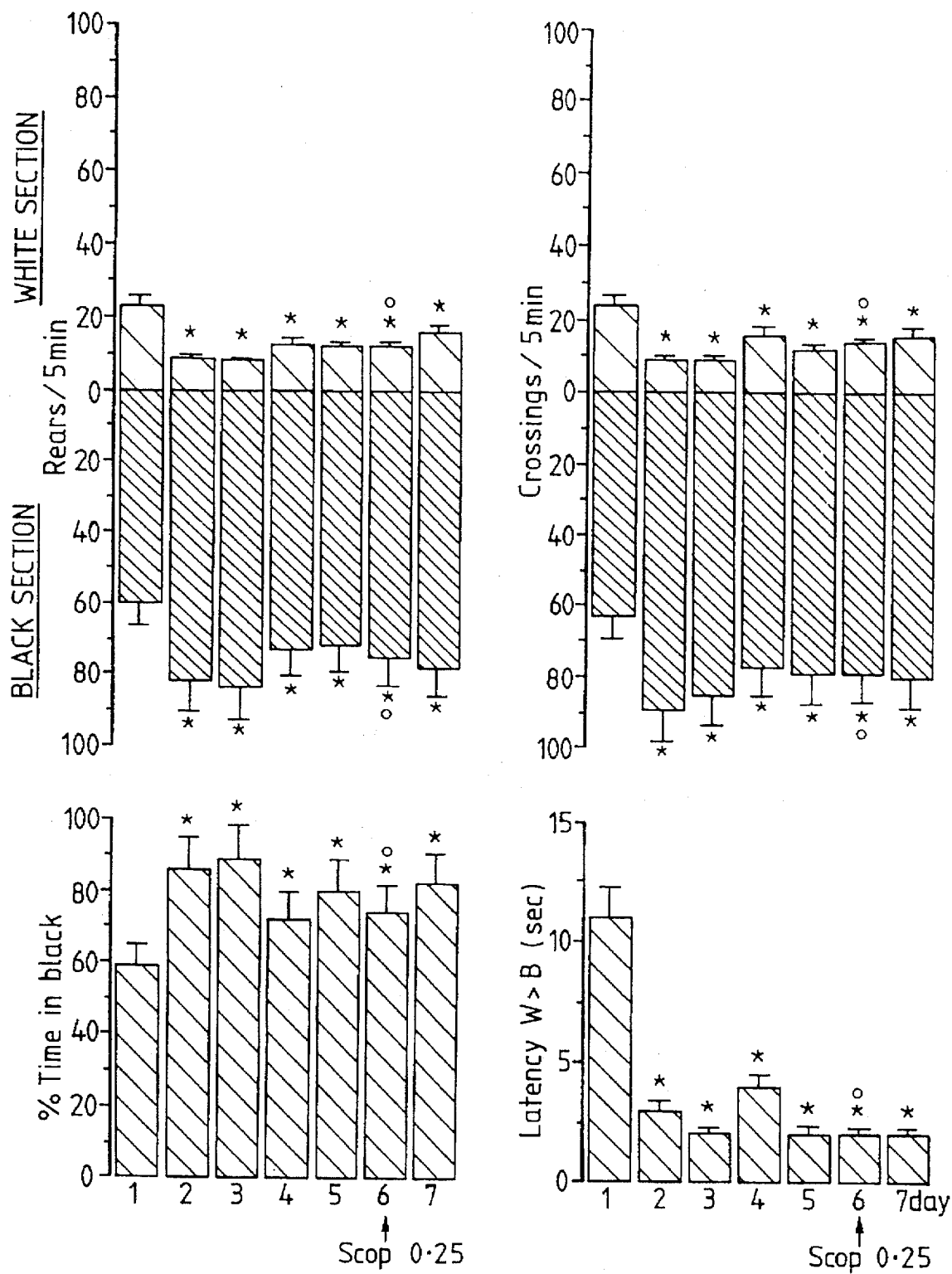

The procedure was then repeated with the compound being given at 1 ng/kg i.p. twice daily (b.d.) throughout the habituation period, the injections being at about 8.00 a.m. (40 minutes before testing) and about 6.00 p.m. FIG. 3 illustrates the ability of the compound to prevent the impairment in habituation caused by the acute scopolamine challenge.

We claim:

1. A compound of formula (I)

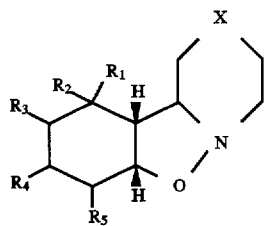

(I)

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, but with the proviso that when each of $R_1$ to $R_5$ is hydrogen X is not >O, the compound optionally being in the form of a salt thereof formed with a physiologically acceptable inorganic or organic acid.

2. A compound according to claim 1, in which X is >NR wherein R is methyl or phenyl.

3. A compound according to claim 1, in which X is >O.

4. A compound according to claim 1, in which $R_1$, $R_4$ and $R_5$ are each hydrogen and $R_2$ and $R_3$ are the second bond of a double bond joining positions 9 and 10.

5. A compound according to claim 1, in which $R_1$ and $R_2$ are an oxo group and $R_3$, $R_4$ and $R_5$ are each hydrogen.

6. A compound according to claim 1 being [cis-1,2,3,4,5,6a,7,8,9,10,10a,10b-dodecahydro-1,4-oxazino[3',4':2,3]benzo-[d]isoxazol-4-one] cis-1,3,4,6a,7,8,9,10,10a,10b-decahydro-1,4-oxazino-[4,3-b]benz[d]isoxazol-10-one or a salt thereof.

7. A compound according to claim 1 being [cis-1,2,3,4,5,6a,7,8,10a,10b-decahydro-1,4-oxazino[3',4':2,3]benzo[d]isoxazole] cis-1,3,4,6a,7,8,10a,10b-octahydro-1,4-oxazino[4,3-b]benz[d]isoxazol or a salt thereof.

8. A compound according to claim 1, in which the hydrogen atom at the 10b position is in the cis configuration relative to the hydrogen atoms at positions 6a and 10a.

9. A pharmaceutical composition comprising a compound of formula (I) as defined in claim 1 together with a pharmaceutically acceptable diluent or carrier.

10. A pharmaceutical composition for treating anxiety or effecting improvement of learning ability and/or the reversal of amnesia comprising a compound of formula (I) as defined in claim 1.

11. A method for treating a patient suffering from a condition requiring an improvement in learning ability or the alleviation of anxiety which comprises administering to said patient a therapeutically effective mount of a compound of a formula (I)

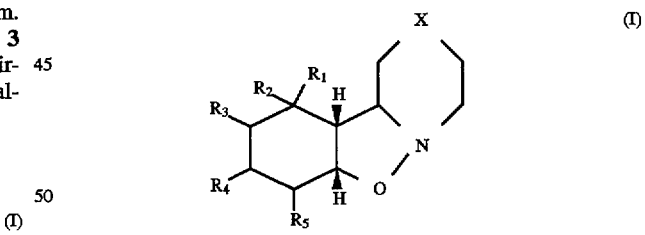

(I)

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, the compound optionally being in the form of a salt thereof formed with a physiologically acceptable inorganic or organic acid.

12. A method for treating a patient suffering from anxiety which comprises administering to said patient a therapeutically effective amount of a compound of formula I.

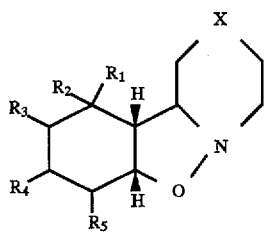

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, the compound optionally being in the form of a salt thereof formed with a physiologically acceptable inorganic or organic acid.

13. A method for the treatment of a patient requiring improvement of learning ability and/or the reversal of amnesia which comprises the step administering to said patient a therapeutically effective amount of a compound of formula (I)

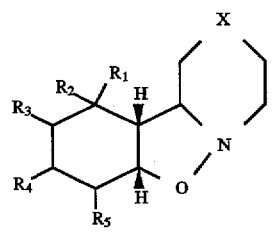

in which X represents a group >O, >S, >C=O or >NR wherein R is hydrogen, $C_{1-6}$ alkyl, phenyl or $C_{7-12}$ phenalkyl, $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, the compound optionally being in the form of a salt thereof formed with a physiologically acceptable inorganic or organic acid.

14. A method of preparing an anxiolytic agent or an agent for effecting improvements in learning behavior, which comprises the steps of:

reacting a compound of formula (II):

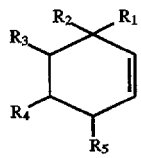

in which $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, with a compound of formula (III):

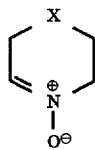

wherein X represents a group >O, >S, >C=O or >NR wherein R is hydrogen, $C_{1-6}$ alkyl, phenyl or $C_{7-12}$ phenalkyl, with the proviso that when each of $R_1$ to $R_5$ is hydrogen, X is not O.

15. A method of preparing an anxiolytic agent, which comprises the steps of:

reacting a compound of formula (II):

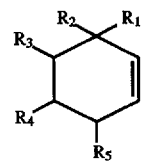

in which $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing -hydrogen, with a compound of formula (III):

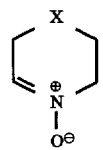

wherein X represents a group >O, >S, >C=O or >NR wherein R is hydrogen, $C_{1-6}$ alkyl, phenyl or $C_{7-12}$ phenalkyl, with the proviso that when each of $R_1$ to $R_5$ is hydrogen, X is not O.

16. A method of preparing an agent for effecting improvements in learning behavior, which comprises the steps of:

reacting a compound of formula (II):

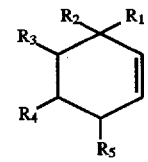

in which $R_1$ and $R_2$ each represent hydrogen or together represent an oxo group and $R_3$, $R_4$ and $R_5$ each represent hydrogen or $R_1$ represents hydrogen and two of $R_2$, $R_3$, $R_4$ and $R_5$ together represent the second bond of a double bond joining positions 7 and 8, 8 and 9 or 9 and 10 with the remaining two of $R_2$, $R_3$, $R_4$ and $R_5$ representing hydrogen, with a compound of formula (III):

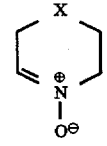

wherein X represents a group >O, >S, >C=O or >NR wherein R is hydrogen, $C_{1-6}$ alkyl, phenyl or $C_{7-12}$ phenalkyl, with the proviso that when each of $R_1$ to $R_5$ is hydrogen, X is not O.

17. A method according to claim 14, wherein the compound of formula (III) is formed in situ from a compound of formula (IIIa):
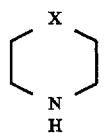 (IIIa)
wherein X is as defined in claim 20, and converting the compound of formula (IIIa) to the compound of formula (III) by a tungstate catalyzed oxidation.
* * * * *